United States Patent
Hansmann et al.

(10) Patent No.: US 11,592,426 B2
(45) Date of Patent: Feb. 28, 2023

(54) METHOD FOR DETERMINING THE LOGARITHMIC REDUCTION VALUE LRV OF A SIZE EXCLUSION FILTER

(71) Applicant: Sartorius Stedim Biotech GmbH, Göttingen (DE)

(72) Inventors: Björn Hansmann, Göttingen (DE); Marcus Peiker, Mietingen (DE); Volkmar Thom, Göttingen (DE)

(73) Assignee: Sartorius Stedim Biotech GmbH

( * ) Notice: Subject to any disclaimer, the term of this patent is extended or adjusted under 35 U.S.C. 154(b) by 1183 days.

(21) Appl. No.: 16/091,489

(22) PCT Filed: Apr. 21, 2017

(86) PCT No.: PCT/EP2017/000513
§ 371 (c)(1),
(2) Date: Oct. 4, 2018

(87) PCT Pub. No.: WO2017/186346
PCT Pub. Date: Nov. 2, 2017

(65) Prior Publication Data
US 2019/0120802 A1    Apr. 25, 2019

(30) Foreign Application Priority Data

Apr. 26, 2016    (DE) .................... 10 2016 005 049.7

(51) Int. Cl.
*G01N 30/86*    (2006.01)
*B01D 65/10*    (2006.01)
(Continued)

(52) U.S. Cl.
CPC ......... *G01N 30/8617* (2013.01); *B01D 61/16* (2013.01); *B01D 65/10* (2013.01);
(Continued)

(58) Field of Classification Search
CPC . G01N 30/8617; G01N 30/8693; G01N 33/53
See application file for complete search history.

(56) References Cited

U.S. PATENT DOCUMENTS 7,118,675 B2    10/2006    Siwak et al.
7,462,283 B2 *  12/2008    Kelly ................. B01D 67/0093
                                                          210/500.39
(Continued)

FOREIGN PATENT DOCUMENTS

DE    102011105525 A1    12/2012
WO    WO2007/039069       4/2007
WO    WO2010/098867       9/2010

OTHER PUBLICATIONS

Genest, P., et al., "Artifacts of Virus Filter Validation," *BioProcess International*, 11(5):54-61 (May 2013).
(Continued)

*Primary Examiner* — Bryan Bui
(74) *Attorney, Agent, or Firm* — Klarquist Sparkman, LLP

(57) ABSTRACT

The present invention relates to a method for determining the logarithmic reduction value LRV of a size-exclusion filter for a particle of a process solution, which particle is to be clarified, the size-exclusion filter being protected from a blocking adsorbing species present in the process solution by a process adsorber which is connected upstream in series.

7 Claims, 4 Drawing Sheets

Figure 1:
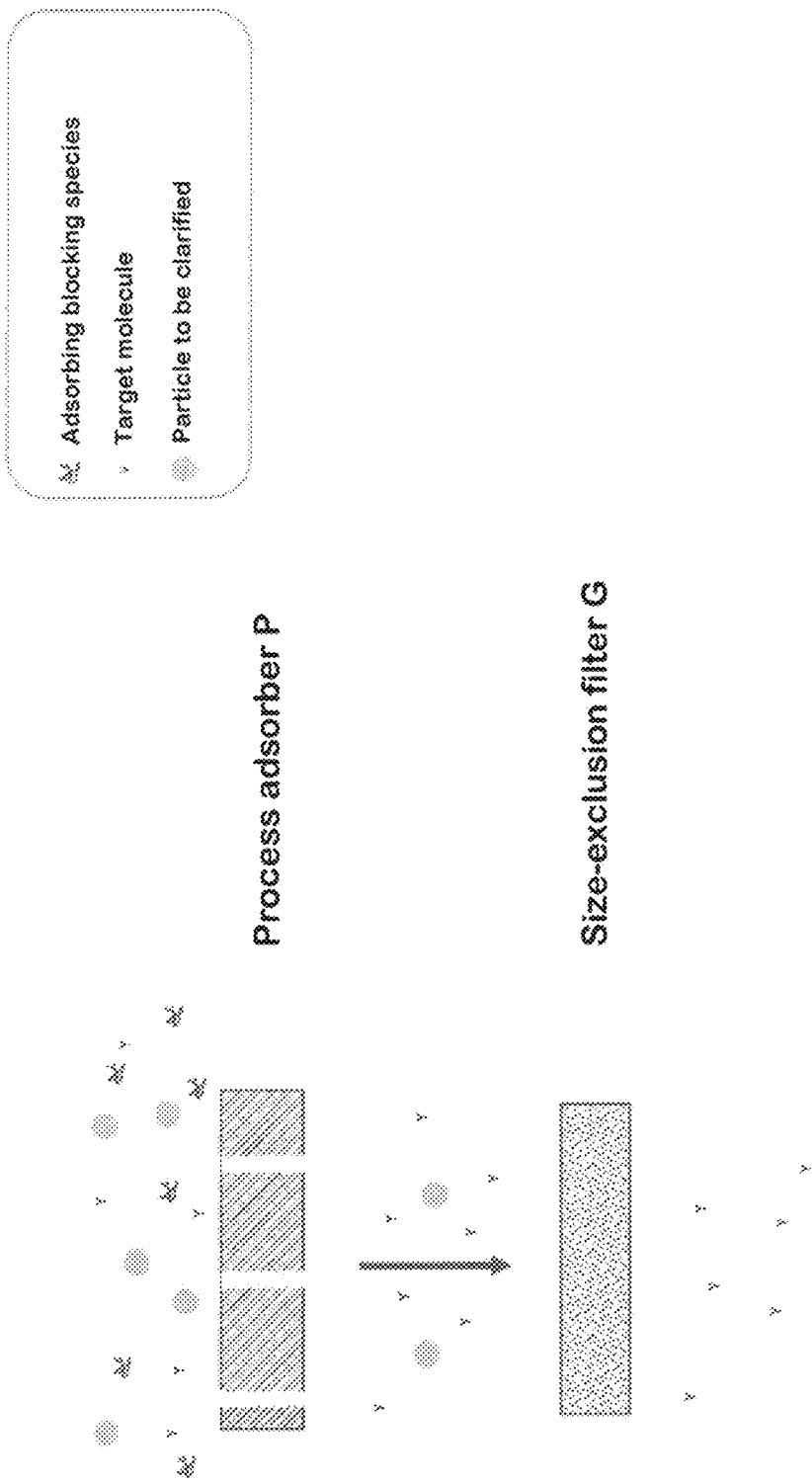

(51) Int. Cl.
　　　*B01D 61/16*　　(2006.01)
　　　*G01N 33/53*　　(2006.01)
　　　*B01D 71/56*　　(2006.01)
　　　*B01D 61/58*　　(2006.01)
　　　*B01D 71/68*　　(2006.01)

(52) U.S. Cl.
　　　CPC ......... *G01N 30/8693* (2013.01); *G01N 33/53* (2013.01); *B01D 61/58* (2013.01); *B01D 71/56* (2013.01); *B01D 71/68* (2013.01); *B01D 2311/04* (2013.01); *B01D 2317/025* (2013.01); *G01N 2030/862* (2013.01)

(56) References Cited

U.S. PATENT DOCUMENTS

| | | | | |
|---|---|---|---|---|
| 9,644,187 | B2* | 5/2017 | Asher | ................ C12N 7/00 |
| 2012/0088228 | A1 | 4/2012 | Asher et al. | |
| 2015/0013434 | A1 | 1/2015 | Hong et al. | |

OTHER PUBLICATIONS

International Search Report and Written Opinion for PCT/EP2017/000513 (dated Nov. 2, 2017) (w/English International Search Report).

Ireland, T. et al., "Optimizing Virus Filter Performance with Prefiltration," *BioProcess International*, 3: 44-47 (Nov. 2005).

Metzger, M. et al., "Evaluating Adsorptive Filtration as a Unit Operation for Virus Removal," *BioProcess International*, 13(2):36-44 (Feb. 2015).

Ruppach, H., "$Log_{10}$ Reduction Factors in Viral Clearance Studies," *BioProcessing Journal*, 12(4):24-30 (Jan. 2014).

Shukla, A., et al. "Viral clearance for biopharmaceutical downstream processes," *Pharmaceutical Bioprocessing*, 3(2):127-138 (Apr. 2015).

Tipton, B. et al., "Retrovirus and Parvovirus Clearance form an Affinity Column Product Using Adsorptive Depth Filtration," *BioPharm*, 15(9):43-50 (Sep. 2002).

* cited by examiner

METHOD FOR DETERMINING THE LOGARITHMIC REDUCTION VALUE LRV OF A SIZE EXCLUSION FILTER

CROSS REFERENCE TO RELATED APPLICATIONS

This is the U.S. National Stage of International Application No. PCT/EP2017/000513, filed Apr. 21, 2017, which in turn claims the benefit of German Application No. 10 2016 005 049.7, filed Apr. 26, 2016, which application is incorporated herein in its entirety.

BACKGROUND

Field of the Invention

The present invention relates to a method for determining the logarithmic reduction value LRV of a size-exclusion filter for a particle of a process solution, which particle is to be clarified, the size-exclusion filter being protected from a blocking adsorbing species present in the process solution by a process adsorber which is connected upstream in series.

Description of the Related Art

In the (bio)pharmaceutical industry, the results from virus-depletion studies are an integral part of the authorization dossier and thus vital for the demonstration of the drug safety of products which are produced in mammalian cells. In this connection, the depletion of viruses is, for example, done from protein solutions containing both protein monomers and protein aggregates. Both in the virus-depletion studies and on the production scale, use is usually made of a combination of a prefilter (process adsorber), which retains both the protein aggregates in an adsorptive manner and the viruses according to the principle of size exclusion, and a virus filter, which only retains the viruses according to the principle of size exclusion. In a virus-depletion study, this (undesired) virus retention by the prefilter can lead to the virus retention achieved by the virus filter appearing higher than it would actually be if the virus retention of the virus filter alone were investigated. Thus, it has hitherto not been possible in the prior art to make a precise distinction between the virus retention due to the prefilter and to the virus filter.

SUMMARY

In some embodiments, the present invention relates to a method for determining the logarithmic reduction value LRV of a size-exclusion filter for a particle of a process solution, which particle is to be clarified, the size-exclusion filter being protected from a blocking adsorbing species present in the process solution by a process adsorber which is connected upstream in series.

FIGURES

FIG. 1 shows a production-scale filtration system comprising a process adsorber P and a size-exclusion filter G.

FIG. 2 shows a production-scale filtration system (left) and a test system (right).

FIG. 3 shows the result of Example 1 for gold nanoparticles.

FIG. 4 shows the result of Example 1 for latex beads.

FIG. 5 shows the results of the filtrations from Example 3.

FIG. 6 shows the results of the filtrations from Example 3.

DETAILED DESCRIPTION OF THE INVENTION

For the most part, virus-depletion studies are carried out in specialized companies, known as contract laboratories. To this end, it is generally necessary to send the starting materials for the individual process steps to the contract laboratories. In many cases, shipping is done under deep-frozen conditions (−20° C./−70° C.). Where freezing is not possible because of product stability (aggregate formation), shipping is done under cooled conditions (2 to 8° C.).

The "freezing/thawing" method tends to promote or even intensify the formation of aggregates of the target product or else of secondary products as well in the process solution. By implication, these are artifacts which are not to be found in the GMP process (good manufacturing practice process) through the direct further processing of the process intermediates. In order to be able to use the thawed process solution as "representative" in the virus study, said aggregates must be depleted by a prefiltration via a prefilter, known as process adsorber.

In the "virus filtration" process step, the formation of aggregates in the actual process as well is undesired, since the aggregates can block the narrow-pore virus filter membranes (size-exclusion membranes) and the performance (flow rate/filtration capacity/service life) of the (size-exclusion) filter is thus greatly impaired.

A prefiltration via a process adsorber during the virus studies is thus imperative, either as part of the process management for "difficult-to-filter solutions" or else owing to the circumstance of correction after "freezing/thawing".

For the cases in which the prefiltration serves to deplete the aggregates formed during "freezing/thawing", the risk of blocking the actual virus filter (size-exclusion filter) is already averted by a prefiltration carried out "off-line" if, in these cases, the process solution does not tend, of its own accord, to re-form aggregates.

However, the procedure in the case of "difficult-to-filter solutions" requires that the prefiltration also be done "in-line" as part of the virus study if the process solution, after a prefiltration carried out "off-line" as part of a virus study, has sufficient time once more to form aggregates. However, said "in-line" prefiltration is incompatible with the established approach in virus studies in their current form.

Adsorbing materials are usually used as prefilters (process adsorbers). Such adsorbing materials are used in a wide variety of sectors in industry for achieving separations on the basis of specific or nonspecific adsorption. In this connection, adsorption is a surface phenomenon. In many cases, porous materials are used as adsorptive prefilters, since what they provide, on a small, compact outer form, is a large inner surface accessible for a binding impurity. Said porous materials are inter alia characterized by a pore size which has an effect on the separation property of the material on the basis of size exclusion. There is firstly the difficulty of providing a large surface for binding and of maintaining a compact outer form, but secondly the difficulty of selecting the pore size such that no significant size exclusion of viruses can be demonstrably observed on the prefilter in the case of use in a virus-depletion study. This is only possible to an insufficient extent with a pore size which is used for the production scale and, at the same time, for the virus-depletion study.

In the context of the present invention, size-exclusion properties are all properties which serve for a mechanical separation on the basis of the size, i.e., longitudinal or voluminal extent, of particles. It is characteristic of shaped bodies or devices which have size-exclusion properties that a particle separation limit can be defined on the basis of sample particles. The particle separation limit is defined by the diameter of sample particles which are retained to a defined proportion of the concentration or number. A typical definition of a particle separation limit is the 90% cut-off. Depending on the required sample size, shaped bodies of a narrowest possible size distribution or suitable molecules for the determination of the particle separation limit are used. In the case of molecular particles, the molecular weight is used as an alternative to a diameter.

A description as to how adsorptive prefilters are used in the prior art and as to what is to be understood to be meant by adsorptive prefilters (process adsorbers) in the context of the present application is, for example, found in DE 10 2011 105 525 A1. It is disclosed therein that a shaped body composed of a polyamide can be used in a method which removes biopolymers and viruses from a fluid. A different method, disclosed in U.S. Pat. No. 7,118,675 B2, describes the use of charged and/or modified membranes or depth-filter materials containing diatomaceous earth that are used for the removal of aggregates prior to the virus-depleting filtration. However, none of the above applications explores the issue of use in the depletion study and none solves the problem which arises when using these methods as a result of the prefilter virus depletion not defined in detail.

The problem which arises owing to impurities of the solution in a virus-depletion study, namely that the scaling of the filter areas differs systematically between the virus-depletion study and the production scale, is described in US 2012/088228 A1. Here, it is disclosed that it is possible to minimize impurities from the virus stock solution and to increase the concentration of the stock solution by carrying out an ultracentrifugation and an adsorption step on a cation exchanger or, in general, a chromatographic purification step. The materials described therein for the chromatographic purification largely correspond to the materials also mentioned in U.S. Pat. No. 7,118,675 B2. In addition, chromatographic columns are also explicitly mentioned as media. However, when using the method from US 2012/088228 A1, what is not solved is the problem that the impurities can also originate from the process solution and are removed on the production scale by adsorbing prefilters, the use of which is not possible "in-line" in the virus-depletion study.

A virus-depletion study with a prefiltration done "in-line" can, for example, be carried out as follows:
optional: thawing of the (deep-)frozen process solution
aliquoting of the process solution
addition of the virus stock solution in a predefined ratio ("spike ratio" in [% (v/v)])
depending on the species/size of the added virus, a process-independent prefiltration is carried out in order to make sure that the added virus particles are present in a "monodisperse" manner, i.e., without virus aggregates. For example, a prefiltration is carried out with a size-exclusion filter with 0.45 µm pore size for the model virus MuLV (murine leukemia virus, 80-120 nm), and a 0.1 µm size-exclusion filter is used for representatives of the parvoviruses (e.g., PPV or MVM; 18-24 nm).
reduction of the sample "load" by employees of the contract laboratory in order to be able to determine the starting value of the virus concentration.
performance of the virus filtration using an "in-line" integrated prefilter (process adsorber) upstream of the actual virus filter (size-exclusion filter).
reduction of the sample "filtrate" by employees of the contract laboratory in order to be able to determine the final value of the virus concentration after the virus filtration.

A requirement by the regulatory authorities (e.g., ICH Guideline Q5A (R1), page 8, 2nd paragraph) is that the mechanisms of action of the individual virus-depleting process steps must be known and unambiguously identified. The simultaneous use of multiple steps for virus depletion, for example by a combination of adsorption and size exclusion, is undesired, since, in this case, the depletion cannot, as required by regulations, be attributed to a defined mode of action. Usually, the virus depletion when using an isolated size-exclusion filter is done via the mechanism of size exclusion. However, in the case of the above-described method, the mechanism is unclear, since both adsorption and size exclusion can make a contribution here.

Furthermore, orthogonal methods for depletion are required in the entire process of producing biological pharmaceuticals. Here, orthogonal relates to the underlying mode of action of the method for depletion. For instance, although a depletion could also be shown by the serial performance of the same method, the summation of the shown depletions would probably overestimate the actual value.

This assumption is based on the fact that a population of viruses can be definitely heterogeneous with regard to their properties, which are crucial for the depletion using a specific method. For example, the affinity of the viruses for an adsorber can, even within the same virus species, be heterogeneous to such an extent that the depletion leads to a selection. This preselected virus population will behave differently in a further adsorption step than in the first step.

A central requirement of virus-depletion studies is scalability. Although it is not technically possible to carry out studies on the actual production scale, it ought to be represented as accurately as possible in the studies. The representation of the production scale in the case of use of adsorptive prefilters (process adsorbers) used successfully and advantageously on the production scale is only possible to a limited extent in the methods known to date. In particular, in the hitherto known prior art, there is the problem that, when using upstream process adsorbers, it is frequently not possible to make a distinction between a separation on the basis of the adsorbing properties and on the basis of the size-exclusion properties.

It is therefore an object of the present invention to provide a method for determining the logarithmic reduction value (LRV) of a size-exclusion filter which is protected from a blocking adsorbing species by a process adsorber connected upstream in series, which method makes it possible to separate the two separation mechanisms "adsorption" and "size exclusion" from one another in order to thus be able to achieve a more realistic representation of the production scale in a laboratory-scale virus-depletion study.

Therefore, the present invention provides a method for determining the logarithmic reduction value $LRV_{Size-exclusion\ filter}$ of a size-exclusion filter G for a particle of a process solution, which particle is to be clarified, the size-exclusion filter G being protected from a blocking adsorbing species present in the process solution by a process adsorber P connected upstream in series and the particle to be clarified being retained by the process adsorber P with an $LRV_{Process\ adsorber}$ of 0.5 or more, comprising the steps of:

(a) providing a test system comprising
a size-exclusion filter G, the $LRV_{Size-exclusion\ filter}$ of which is to be determined, and a test adsorber T which is connected upstream of the size-exclusion filter G in series and which consists of a similar material to the process adsorber P and by means of which the particle to be clarified is retained with a known $LRV_{Test\ adsorber}$ of 2 or less, where $LRV_{Test\ adsorber} < LRV_{Process\ adsorber}$;
(b) determining $LRV_{Test\ system}$ of the test system for the particle to be clarified; and
(c) calculating $LRV_{Size-exclusion\ filter}$ by subtracting the $LRV_{Test\ adsorber}$ from $LRV_{Test\ system}$.

According to the present invention, the logarithmic reduction value LRV is defined as the logarithm of the quotient of the concentration "$C_{feed}$" of a substance in a process solution that is to be removed ("feed solution") before passage through a filter and of the concentration "$C_{filtrate}$" of a substance in the process solution that is to be removed after passage through the filter (i.e., in the filtrate), i.e., $$LRV = \log \frac{C_{feed}}{C_{filtrate}}.$$

According to the invention, the term "process solution" is not subject to any particular restriction and refers in particular to an aqueous solution (e.g., a protein solution) which comprises a blocking adsorbing species (e.g., biopolymers and/or polypeptides), a particle to be removed (e.g., viruses) and a target molecule (e.g., monoclonal or polyclonal antibodies, a recombinant protein or products from blood and blood plasma such as albumin, immunoglobulins, coagulation factors and other proteins or polypeptides which are present in blood, blood plasma or in the interior of eukaryotic cells).

The method according to the invention makes it possible to determine the $LRV_{Size-exclusion\ filter}$ of a size-exclusion filter G for a particle of a process solution, which particle is to be clarified, in a filtration system which comprises the size-exclusion filter G and a process adsorber P connected upstream in series. The process adsorber connected upstream in series is required in said filtration system in order to protect the size-exclusion filter G from the blocking adsorbing species present in the process solution. In this connection, the process adsorber P itself already retains the particle to be clarified with an $LRV_{Process\ adsorber}$ of 0.5 or more, i.e., at least 68.4% of the particles to be clarified are already removed from the process solution by the process adsorber P. Advantageously, it is possible via the method according to the invention to determine the $LRV_{Size-exclusion\ filter}$ of the size-exclusion filter G for the particle to be removed, even though in regular operation (i.e., on the production scale) a portion of the species to be clarified is already removed from the process solution by the process adsorber P (see FIG. 1).

According to the invention, the prefiltration by the process adsorber or the test adsorber is carried out "in-line", meaning that it satisfies the guideline of the mechanism of the virus depletion being unambiguously identified.

In step (a) of the method according to the invention, what is provided is a test system comprising the size-exclusion filter G, the $LRV_{Size-exclusion\ filter}$ of which is to be determined, and a test adsorber T connected upstream of the size-exclusion filter G in series. In this connection, the test adsorber T consists of a similar material to the process adsorber P, i.e., test adsorber T and process adsorber P consist of the same base material (such as, for example, polyethersulfone (PES), polyamide (PA), polypropylene (PP), etc.).

According to the invention, test adsorber T retains the particle to be clarified with a known $LRV_{Test\ adsorber}$ of 2 or less, where $LRV_{Test\ adsorber} < LRV_{Process\ adsorber}$, i.e., the test adsorber T retains fewer particles to be clarified than the process adsorber P.

The exact $LRV_{Test\ adsorber}$ of the test adsorber T is known for the specific process conditions of the method according to the invention (e.g., from data from the manufacturer of the test adsorber), or is determined in an optional step before step (a) for the specific process conditions, i.e., depending on the particle to be clarified, the pH and the salt concentration of the solution to be clarified, etc. For example, this is done by determining the concentration of the particle to be clarified in the process solution before passage through the test adsorber ("$C_{feed}$") and the concentration of the particle to be clarified in the process solution after passage through the test adsorber ("$C_{filtrate}$") and calculating the logarithm from the quotient of these variables, as described above. The above-described determination of the $LRV_{Test\ adsorber}$ is preferably done on a test adsorber T which has not yet been fitted into the test system of the method according to the invention.

Consequently, before step (a), the method according to the invention optionally comprises step (a') of determining the $LRV_{Test\ adsorber}$ of the test adsorber T for the process-solution particle to be clarified, the test adsorber T in step (a') being either identical in construction (e.g., same batch) or identical (further use, for example after regeneration) to the test adsorber T of the test system in step (a) of the method according to the invention.

In step (b) of the method according to the invention, the $LRV_{Test\ system}$ of the test system is determined for the particle to be clarified.

In step (c) of the method according to the invention, the $LRV_{Size-exclusion\ filter}$ is calculated by subtracting the $LRV_{Test\ adsorber}$ from $LRV_{Test\ system}$, i.e., $LRV_{Size-exclusion\ filter} = LRV_{Test\ system} - LRV_{Test\ adsorber}$.

The present invention is based on the finding that the $LRV_{Size-exclusion\ filter}$ of a size-exclusion filter G for a particle of a process solution, which particle is to be clarified, in a production-scale filtration system, in which a process adsorber P connected upstream in series is required for protecting the size-exclusion filter G from a blocking adsorbing species, can be determined by carrying out experiments on a test system having the same size-exclusion filter G (i.e., having an identical "cut-off" value, but in smaller sizing) which is also protected in the same manner from the blocking adsorbing species by a prefilter (test adsorber T), the test adsorber T of the laboratory-scale test system allowing, however, a sufficiently large quantity ($LRV_{Test\ adsorber} \leq 2$) of particle to be clarified to pass through owing to larger pores.

Figure 2:
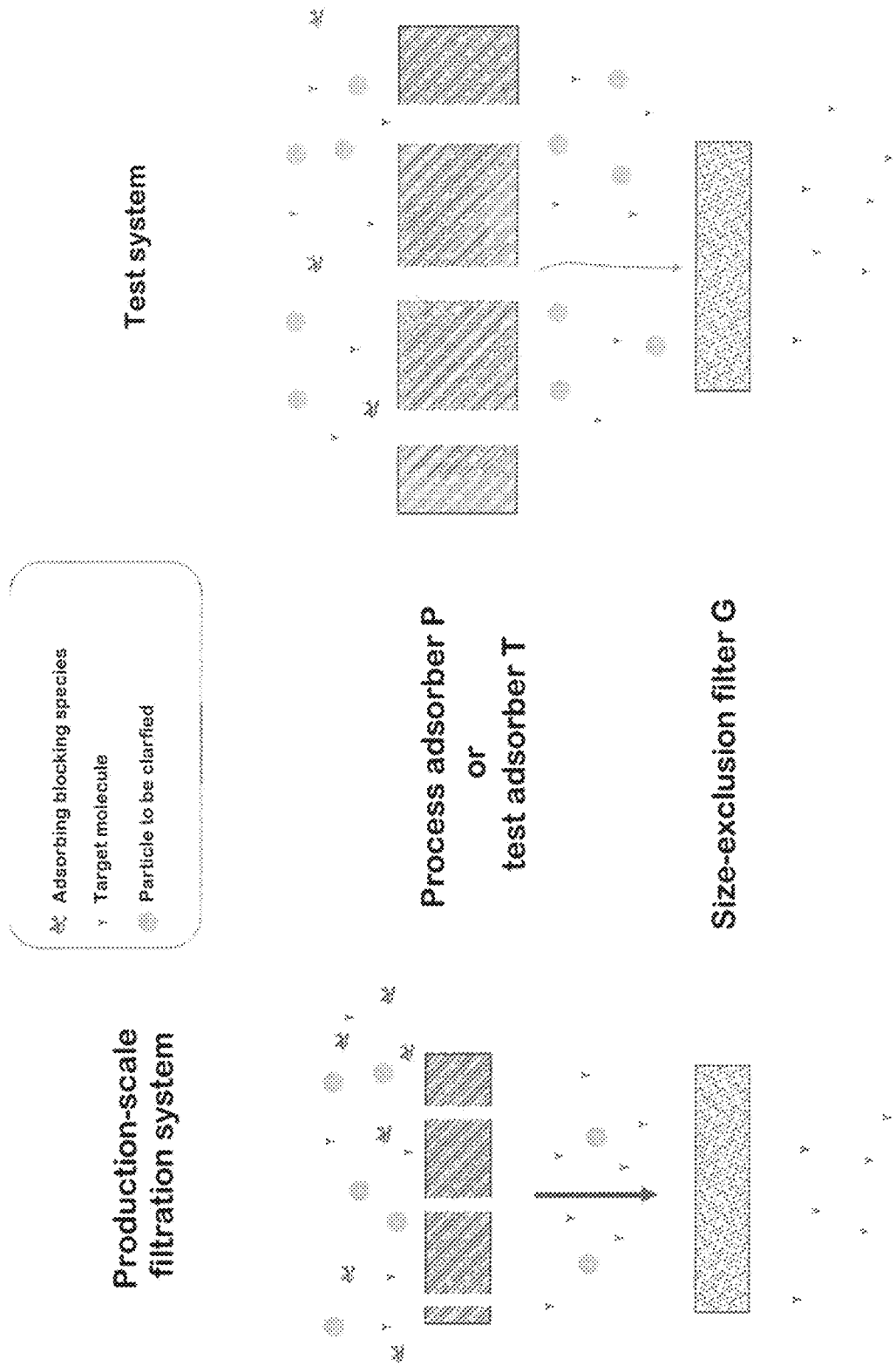

The larger the quantity of particle to be clarified that the test adsorber T of the test system allows to pass through unhindered, the more reliable the determination of the logarithmic reduction value $LRV_{Size-exclusion\ filter}$ of the size-exclusion filter G for the process-solution particle to be clarified. Consequently, according to a preferred embodiment of the present invention, the test adsorber T has an $LRV_{Test\ adsorber}$ of 1.5 or less, more preferably 1.0 or less, and even more preferably 0.5 or less. Most preferably, the test adsorber T has an $LRV_{Test\ adsorber}$ of toward "0" or exactly "0", since, in this case, (approximately) all process-solution particles to be clarified pass through the test adsorber unhindered, the size-exclusion filter G continuing to be protected from the blocking adsorbing species (see FIG. 2).

Adsorbers, i.e., process adsorber and test adsorber, which can be used in the method of the present invention are, in general, materials which, on their outer and inner surface, can chemically or physically bind, i.e., immobilize, substances by means of specific chemical groups attached on the surface (so-called ligands). Examples of said adsorbers having ligands are the charged and/or modified membranes as described in U.S. Pat. No. 7,118,675 B2, and additionally typical chromatographic media such as gels, monoliths, beads and other column materials composed of polymeric support materials or inorganic support materials, such as, for example, silica gel, kieselguhr or aluminum oxide, to which ligands have been applied or which bear ligands as a result of their manufacture. Furthermore, the adsorbers of this invention also mean materials which, in their properties on the outer or inner surface, do not differ from the properties as a whole (i.e., contain no ligands) and likewise have the property of immobilizing substances on their surface under suitable conditions. This class of adsorbers includes, for example, the materials described in DE 10 2011 105 525 A1, more particularly membranes which have adsorbing properties and which, in their properties on the outer or inner surface, do not differ from the properties as a whole. Furthermore, materials such as diatomaceous earth, silica gel, kieselguhr, activated carbon and mineral earths, nano-structured sorption materials and earths, as described in US 2010/0100027 A1, are adsorbers in the context of this invention.

In preferred embodiments of the present invention, use is made of adsorbers present as mechanically integral shaped bodies, i.e., adsorbers which are not bulk fillings. A particularly preferred embodiment is the realization of the adsorber as a porous shaped body in the form of a membrane.

The process adsorber P of the method according to the invention has a specific adsorption capacity $k_1$ for the blocking adsorbing species, is present on a scale $M_1$ and thus has a total adsorption capacity of $k_1 \times M_1$ for the blocking adsorbing species. Similarly, the test adsorber T has a specific adsorption capacity $k_2$ for the blocking adsorbing species, is present on a scale $M_2$ and thus has a total adsorption capacity of $k_2 \times M_2$ for the blocking adsorbing species.

According to a preferred embodiment of the present invention, $$0.1 < \frac{k_1 M_1}{k_2 M_2} < 10,$$

since, in this case, the total adsorption capacities of the process adsorber P and of the test adsorber T for the blocking adsorbing species are approximately the same and the test system thus allows very realistic statements about the production-scale filtration system. The more similar the total adsorption capacities of the process adsorber P and of the test adsorber T, the more realistic the mirroring of the production-scale filtration system by the test system. Consequently, more preferably $$0.5 < \frac{k_1 M_1}{k_2 M_2} < 5$$

and most preferably $$0.9 < \frac{k_1 M_1}{k_2 M_2} < 1.1.$$

Binding or immobilizing properties are characteristic of the material of the adsorbers. The quantity of substances which can be bound depends on the availability of molecular binding places. Fundamental work to describe such sorption phenomena, as described and used here, are, for example, found in "S. Brunauer, P. H. Emmett, E. Teller: *Adsorption of Gases on Multimolecular Layers*. In: *J. Am. Chem. Soc.* 60, No. 2, 1938, pages 309-319" or in "Langmuir: *Surface Chemistry*. Nobel Lecture, Dec. 14, 1932. In: *Nobel Lectures, Chemistry* 1922-1941. Elsevier Publishing Company, Amsterdam, 1966". The number of binding sites for a particular sorbent is described macroscopically as the picked-up mass, i.e., adsorbed or immobilized mass, of a sorbent (capacity). In this connection, capacity can also be normalized to the mass or the volume of the adsorber in order to arrive at a scale-independent material constant, at a specific capacity, since the number of binding sites is proportional thereto.

In the context of this invention, it is sufficient to determine capacity using a suitable model of the sorbent. For the scaling method presented here, it is irrelevant whether the determined capacity of the adsorbers exactly corresponds to the quantity of actual sorbent, so long as a constant proportion of the available binding places of the different adsorbers of the same material is represented thereby, i.e., the proportion of the capacity of two adsorbers composed of the same material having different size-exclusion properties can be determined.

According to the invention, the determination of the total adsorption capacities of the process adsorber P and of the test adsorber T is not subject to any particular restriction. In the context of this invention, suitable methods for determining capacity are, for example, the determination of the inner surface area by gas sorption, more particularly according to a Langmuir isotherm or a BET isotherm (Brunauer-Emmett-Teller isotherm).

An alternative method for determining adsorption capacity is determination via a breakthrough curve. In this method, a constant inward flow of a constant concentration of sorbent as component of a mixture of various substances or as pure substance is applied to the adsorber and the concentration or quantity of the sorbent is measured both upstream and downstream of the adsorber. If the concentration downstream of the adsorber reaches 10% of the concentration upstream of the adsorber, the capacity of the adsorber is exhausted and the difference in mass between applied sorbent in the inward flow and the mass of the out-flowing sorbent in the outward flow of the adsorber serves as a measure of the capacity of the adsorber. To identify and to minimize kinetic effects, the breakthrough curve is determined at various inward flow velocities (defined as inward-flowing mass of sorbent per unit of time)

differing by at least a factor of 5. The inward flow velocity is then reduced until the capacity becomes independent of the velocity of the inward flow. For a person skilled in the art, it is evident that it is also sufficient to determine the dynamic capacity for the process parameters actually used for the particular scales which are to be scaled. The method for determining the concentration of the sorbent is carried out according to the nature of the sorbent. A person skilled in the art is aware of the necessary methods; therefore, reference is only made here by way of example to a nonexhaustive selection of established methods: established methods are absorption- or fluorescence-based detections within the region of IR, visible light, UV; detections via refractive index, electrochemical potential on suitable electrodes; detections via conductivity, specific heat, dielectricity and other methods which take into account the composition of the sorbent-containing mixtures and the concentration of the sorbent.

In one embodiment of the present invention, it is also possible to use binding experiments with model proteins in order to determine capacity. In this connection, an established method for determining protein binding is the BCA assay ("BCA" corresponds to 2,2-biquinoline-4,4-dicarboxylic acid disodium salt dihydrate).

A further method is static incubation, i.e., contacting the sorbent with the adsorber and subsequently determining the mass balance of the unbound and bound sorbent. In the case of use of proteins, determination of protein concentration via fluorescence of the groups or determination by means of the absorption of UV light within the range of 270 to 280 nm or at 230 nm wavelength are available for example. The method for balancing the mass of bound or unbound sorbents can be easily selected by a person skilled in the art and is guided by the nature of the sorbent.

According to one embodiment, the test adsorber T has a size-exclusion limit (90% cut-off) of 10 nm or greater, preferably 20 nm or greater and particularly preferably 50 nm or greater, since particularly preferred test particles are viruses sized from 100 to 200 nm.

Size-exclusion filters in the context of the present invention are microfilters and ultrafilters as defined in *Pure Appl. Chem.*, 1996, 68, 1479. In this connection, a relevant microfiltration is defined as a pressure-driven membrane-based separation method in which particles and dissolved macromolecules larger than 0.1 µm are retained. By contrast, ultrafiltration is defined as a pressure-driven membrane-based separation method in which particles and dissolved macromolecules smaller than 0.1 µm and larger than about 2 nm are retained. Possible materials for size-exclusion filters are, for example, polymers composed of cellulose, cellulose derivatives such as cellulose acetate and cellulose nitrate, polypropylene, polyethylene, polyether ketones, polyvinylidene fluoride, polysulfones, polyethersulfones, aromatic and aliphatic polyamides, ceramics such as $Al_2O_3$, silicates, nitrides, borides and mixtures of these substances, i.e., materials from which porous, mechanically integral shaped bodies can be produced. In the method according to the invention, the size-exclusion limit (90% cut-off) of the size-exclusion filter is smaller than the size-exclusion limit (90% cut-off) of the test adsorber. According to a preferred embodiment, the size-exclusion limit (90% cut-off) of the size-exclusion filter is smaller than 1 µm, more preferably smaller than 200 nm and particularly preferably from 50 nm to 2 nm.

According to the invention, the blocking adsorbing species from which the size-exclusion filter G is to be protected by the process adsorber P or test adsorber T connected upstream in series is not subject to any particular restriction. For example, the blocking adsorbing species is at least one member of the group consisting of biopolymers (e.g., proteins, DNA and RNA, constituents of extracellular matrices such as polysaccharides), biopolymer aggregates (e.g., protein aggregates, pure-substance aggregates of the aforementioned biopolymers and mixed aggregates of the same), biological particles (e.g., microorganisms such as bacteria and mycoplasmas).

Advantageously, the method according to the invention can be used for small-scale representation and analysis of production-scale virus-depletion studies. In particular, the method according to the invention makes it possible, in contrast to the methods known from the prior art, to quantitatively distinguish between the virus retention due to the prefilter and the virus retention brought about by the virus filter. As a result, it is advantageously possible to determine virus retention in virus-depletion studies in a reliable and precise manner, which virus retention originates solely from the virus filter, without the virus retention value being falsified by the contribution made by the prefilter.

The present invention will be more particularly elucidated on the basis of the following nonrestrictive examples.

EXAMPLES

Example 1: Determination of the Size-Exclusion Limit of Adsorbers

In this exemplary embodiment, microporous membranes composed of polyamide will be used as adsorbers. In said embodiment, "25006" and "25058" are two membranes which have been produced from the same basic substances (base material), but have different size-exclusion properties: "25058" is a process adsorber in the context of this invention, "25006" is a test adsorber in the context of this invention. The aforementioned materials have the following properties:
25006: polyamide adsorber, nominal pore size 0.45 µm,
25058: polyamide adsorber, nominal pore size 0.10 µm.

The membranes will be used as filter disks. Fluorescent latex beads will be used as sample particles. The size of the beads will be determined using dynamic light scattering in backscattering mode from the z-average. Determination will be carried out by using zeta sizer nano from Malvern.

Thereafter, the various adsorbers will be used for the filtration of a) gold nanoparticles and b) for the filtration of fluorescent latex beads in order to determine $LRV_{Test\ adsorber}$ and $LRV_{Process\ adsorber}$.

Furthermore, the retention $LRV_{Test\ system}$ of these particles in the test system composed of test adsorber T and size-exclusion filter G will be determined, as described in the method according to the invention in step (b).

For comparison, the retention of these particles in the process system composed of the process adsorber P and the size-exclusion filter G will also be ascertained. The ascertainment of $LRV_{Size-exclusion\ filter}$ from said process system in the following step (c) is not in accordance with the invention, but prior art. In this exemplary embodiment, disadvantages of this hitherto customary type of ascertainment will be shown.

In step (c) of the method according to the invention, the retention of the size-exclusion filter will be determined from the difference $LRV_{Test\ system} - LRV_{Test\ adsorber}$.

In the case of the noninventive calculation according to the prior art, i.e., according to $LRV_{Size-exclusion\ filter} = LRV_{Process\ system} - LRV_{Process\ adsorber}$, disadvantages arise, as will be described later on in the description of the results of this exemplary embodiment.

Description of the determination of particle size and of filtration:

In addition to viruses, nanoparticles are a particle type as to be retained by the size-exclusion filter. In this exemplary embodiment, gold nanoparticles and fluorescently labeled latex particles are used. Polyamide membrane layers (PA membrane layers) are used as adsorbers P and T; the size-exclusion filter is, in this case, a polyethersulfone membrane having a nominal pore size of 20 nm.

Use is made of particles having a 50 nm (gold/Nanopartz; CAS: A11-50-CIT-100; lot: E2451C) and 200 nm (fluorescent latex beads/Thermo Fisher; Fluoro-Max; CAS: G100) nominal size as per manufacturer data. The size of the particles serves as a model for viruses using PA adsorbers of differing pore size.

To verify the monodispersity and size of the particles, it is ascertained using dynamic light scattering.

Determination of the size of the particles on the basis of DLS (dynamic light scattering):

Description of the method:

DLS settings:

Material: latex, or gold

Dispersant: water at 25° C., holding temp. 180 s

Cell type: ZEN0040 (small cuvette)

Measurement: 173° backscatter

Data processing: general purpose (normal resolution)

Triplicate determination with three independent samples of the particle solution yields the following variables:

Gold particles, 50 nm:

z-average: 51.8±0.7 nm

Latex beads, 200 nm:

z-average: 201.6±0.3 nm

The error relates to the statistically determined standard deviation of the three measurements.

Filtration and determination of the particle concentrations in nonfiltrate and filtrate:

The process adsorber P is represented by a layer structure composed of polyamide membranes having a nominal pore size of 0.1 μm.

The test adsorber T is represented by the combination of two different membranes in a layer structure composed of three layers of the polyamide membrane 25005 (0.65 μm nominal pore size) and one layer of the membrane 25006 (0.45 μm nominal pore size).

Gold, 50 nm: detection via UV-VIS

Solution: gold solution containing 0.26% SDS (sodium dodecyl sulfate) having an optical density at 527 nm of about 1

Filtration:

The membrane is preflushed with a 0.26% SDS solution using 50 L/m² (volume per incident-flow area of the adsorber), but at least five times the dead volume of the filtration apparatus.

This is followed by filtering the gold-particle solution. Filtered across the adsorbers are 30 L/m² of the gold-particle solution, but at least three times the dead volume of the filtration apparatus. Thereafter, two samples are collected separately in order to determine the concentration of the particles:

2 fractions per 10 L/m² are collected separately from one another and analyzed for the particle content.

The measurement of the concentration of the particles is done against a calibration curve which is generated from a dilution series of the above-described particle solution.

Gold nanoparticles are quantified via their absorption at 527 nm.

The latex beads are quantified on the basis of their fluorescence. This involves using the following settings:

Solution, 200 nm: 0.5% commercial latex beads solution in RO—H₂O containing 0.26% SDS Gently swirl the latex, then hold for approx. 15 s in an ultrasonic bath.

Filtration:

Flush the membrane with 5 ml of 0.26% SDS solution (Virosart® Max, 0.5 bar; 25006, 0.1 bar)

Flush 3 g containing latex beads solution, then

Collect 2×1 g fractions via a balance (4 ml glass tubes with lid)

Measurement:

Set the spectrometer to fluorescence (clear-bottom black plate "nunc 96Well" CAS: 265301)

Excitation wavelength: 468 nm; emission wavelength: 508 nm

Standard series/%: 100, 75, 50, 25, 0

Measurement volume: 200 μl

Amplification, 200 nm: 86

Figure 3:
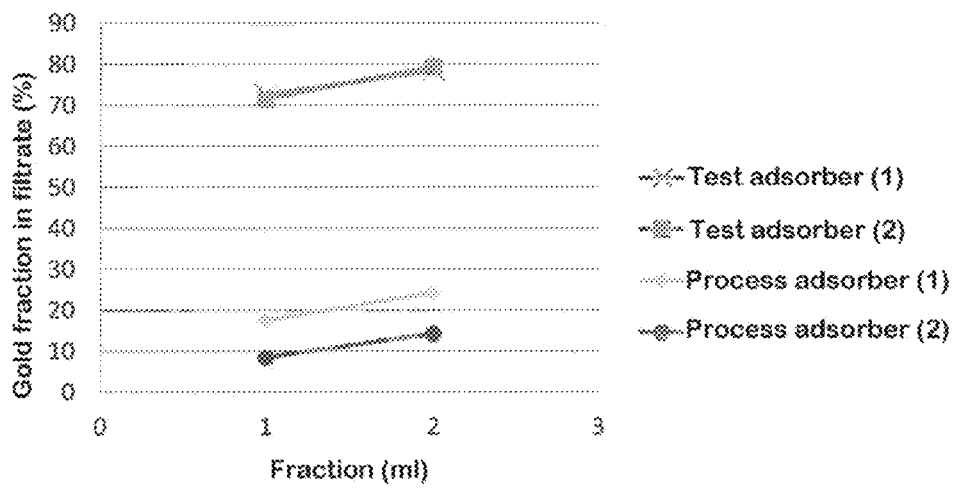

Size-Determination Results:

Gold Filtration (See FIG. 3):

The retention of the Virosart® Max (25058=process adsorber) is, on average, 80%; in the case of the membrane 25005, it is about 25% (test adsorber). The retention for gold nanoparticles where d=50 nm for the membrane 25058 corresponds to an $LRV_{Process\ adsorber} = \log(C_{feed}/C_{filtrate}) = \log (1/0.2) = 0.69$. For the test adsorber, the result is a retention of $LRV_{Test\ adsorber} = \log(C_{feed}/C_{filtrate}) = \log (1/0.75) = 0.12$.

| Determination mode for the concentration of gold nanoparticles | Absorption |
| --- | --- |
| Cuvette | |
| Wavelength | 527 nm |
| Bandwidth | 9 nm |
| Number of flashes | 25 |
| Rest time | 0 ms |

Figure 4:
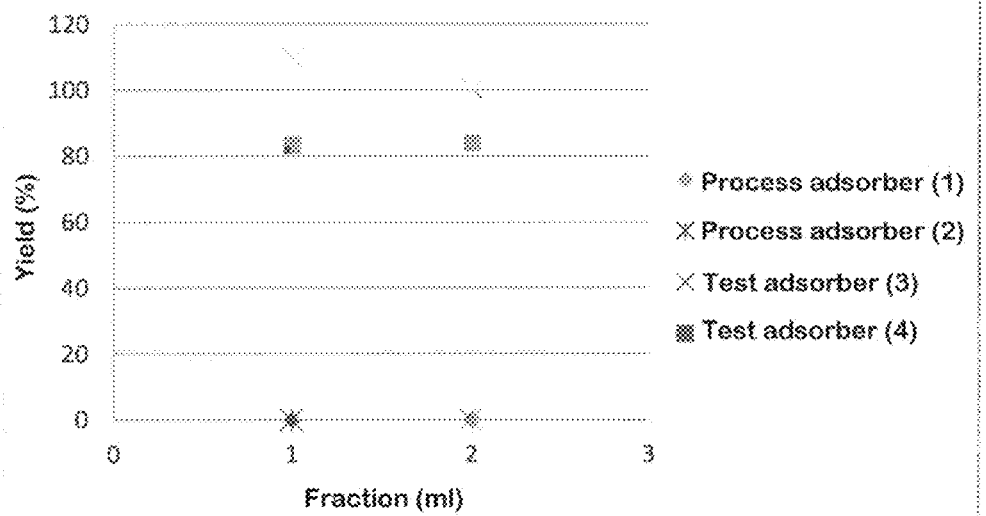

Latex Filtration (See FIG. 4):

200 nm: The retention of the Virosart® Max (25058=process adsorber) is, on average, >99.9%; in the case of the membrane 25005 (test adsorber), it is about 10%. The retention for latex beads of 193 nm in size is, for the process adsorber, a large $LRV_{Process\ adsorber} = \log(C_{feed}/C_{filtrate}) = \log (1/0.001) = 3$. For the test adsorber, the result is an $LRV_{Test\ adsorber} = \log(C_{feed}/C_{filtrate}) = \log(1/0.9) = 0.04$.

| Determination mode for the concentration of latex beads | Fluorescence measurement from above |
|---|---|
| Excitation wavelength | 468 nm |
| Emission wavelength | 508 nm |
| Excitation bandwidth | 9 nm |
| Emission bandwidth | 20 nm |
| Amplification | 86 manual |
| Number of flashes | 25 |
| Integration time | 20 µs |
| Delay time | 0 µs |
| Rest time | 0 ms |
| Plate region | D6-D10; E6-H9 |

According to the invention, the prefiltration by the process adsorber or the test adsorber is carried out "in-line", meaning that it satisfies the guideline of the mechanism of the virus depletion being unambiguously identified.

The retention of the test systems $LRV_{Test\ system}$ is determined for the combination of the test adsorber and, as comparative example, also with the process adsorber for the gold nanoparticles of 50 nm in size and for the latex beads of 193 nm in size. The concentrations of the particles are determined as for the determination of $LRV_{Test\ adsorber}$.

In this exemplary embodiment, the size-exclusion filter used is a Virosart® CPV (polyethersulfone membrane having a nominal pore size of 20 nm) virus filter, available from Sartorius Stedim Biotech GmbH.

The retention of the gold nanoparticles of the two systems is:

$$LRV_{Test\ system}(25005/25006+\text{Virosart® CPV})>3.2$$

$$LRV_{Test\ system}(25058+\text{Virosart® CPV})>3.2$$

The retention of the latex beads of the two systems is:

$$LRV_{Test\ system}(25005/25006+\text{Virosart® CPV})\geq3.2$$

$$LRV_{Test\ system}(25058+\text{Virosart® CPV})\geq3.2$$

Analogous to the ascertainment of the retention of the test adsorbers used and of the process adsorber, the $LRV_{Size-exclusion\ filter}$ is now calculated in step (c) of the method according to the invention by subtracting the $LRV_{Test\ adsorber}$ from $LRV_{Test\ system}$, i.e., $LRV_{Size-exclusion\ filter}=LRV_{Test\ system}-LRV_{Test\ adsorber}$.

For the retention of the size-exclusion filter Virosart® CPV, what thereby arises for the retention of the gold nanoparticles using the adsorber 25058 is:

$$LRV_{Size-exclusion\ filter}=LRV_{Test\ system}-LRV_{Test\ adsorber}(25058)$$

$$LRV_{Size-exclusion\ filter}\geq3.2-0.69$$

$$LRV_{Size-exclusion\ filter}\geq2.51$$

Using the method according to the invention with use of the adsorber 25006/25005, what arises for the retention of the gold nanoparticles is:

$$LRV_{Size-exclusion\ filter}=LRV_{Test\ system}-LRV_{Test\ adsorber}(25006/25005)$$

$$LRV_{Size-exclusion\ filter}\geq3.2-0.12$$

$$LRV_{Size-exclusion\ filter}\geq3.08$$

Analogously, the retention for the latex beads is now determined. For the use of the adsorber 25058, what arises is:

$$LRV_{Size-exclusion\ filter}\geq3.2-3.0$$

$$LRV_{Size-exclusion\ filter}\geq0.2$$

Using the method according to the invention with the adsorber 25006/25005, a higher retention is detected:

$$LRV_{Size-exclusion\ filter}\geq3.2-0.04$$

$$LRV_{Size-exclusion\ filter}\geq3.16$$

Example 2: Determination of the Adsorption Capacity of the Adsorbers from Example 1

Capacity is ascertained on the basis of static protein adsorption using BCA reagent. The redox reaction of the BCA reagent is used for the detection of protein. The color of solutions of the BCA reagent is quantified as absorbance at 562 nm. A calibration curve of known protein concentrations is created and the measurement values are evaluated using this calibration.

DETAILED DESCRIPTION

1. Add 3 ml of γ-globulin solution (3 mg/ml) per Petri dish.
2. Using tweezers, place the individual test samples (13 mm diameter) and reference samples in, in each case, an appropriately labeled Petri dish (3.5 cm), avoiding any direct hand contact. (Direct marking of the samples can—if necessary—be done with an electrophoresis pen).
3. Incubate the samples in a shaker (80/min) for 3 h at room temperature (approx. 20° C.).
4. Using tweezers, remove the samples from the Petri dishes and transfer them to appropriately labeled Petri dishes (10 cm).
5. Add 15 ml of 0.05 M KPi buffer, pH 7.0 per Petri dish and shake for 15 min, then carefully aspirate the buffer solution using a water aspirator and additionally repeat this procedure 3×.
6. Individually transfer the filter samples to appropriately marked Petri dishes (3.5 cm).
7. To create the calibration curve, individually pipette 3×25 µl, 3×50 µl, 3×75 µl, 3×100 µl (calibration samples) and 3×0 µl (=blank sample) samples of γ-globulin solution (1 µg/µl) into appropriately labeled Petri dishes (3.5 cm), add 2000 µl of BCA reagent per dish and immediately place on the shaking platform, then similarly provide the individual membrane samples with 2000 µl of BCA reagent each and shake at room temperature (approx. 20° C.).
8. The photometric measurement of the samples is done in 1 cm semi-microcuvettes. After one hour, the absorbance value of the blank sample at 562 nm is first determined, noted for control purposes and set to zero for the subsequent measurements. Thereafter, the calibration solutions and membrane samples are measured successively without interruption and in the order of their preparation and the absorbance values are noted in the test record.

The adsorption capacities thus ascertained are used to determine the quantity of the adsorbers, in this case as area ratios relative to the process adsorber. The results of the capacity determination and the resulting quantities of the corresponding adsorbers are summarized in Table 1:

TABLE 1

Determination of the binding of IgG at pH = 6 with various adsorbers by means of BCA assay (column: BCA_IVIG) and presentation of the scaling factors between process adsorbers and test adsorbers (column: Area ratio according to BCA).

| Category | Type | Pore size (nominal) [μm] | BCA_IVIG [μg/cm$^2$] | Area ratio according to BCA | Service life of IVIG HC as end filter [l/m$^2$ in 4 h] |
|---|---|---|---|---|---|
| | Polyamide adsorber | | | | |
| Test adsorber | 25004 | 0.8 | 52 | 1.62 | 89 |
| Test adsorber | 25005 | 0.65 | 59 | 1.42 | 91 |
| Test adsorber | 25006 | 0.45 | 71 | 1.18 | 83 |
| Process adsorber | 25058-SF | 0.1 | 84 | 1 | 84 |
| | | | pH = 6 | | pH = 6 |
| | Negative charge: strong cation exchangers AMPS-MBAm) | | | | |
| Test adsorber | modif. 15445 | | 52 | 1.62 | 200 |
| Process adsorber | modif. 15458_3/0.6 | | 87 | 0.97 | 165 |
| Process adsorber | modif. 15458_2/0.4 | | 60 | 1.40 | 134 |
| Reference: without charge modification | 15458 | 0.1 | 3.3 | 25.45 | |
| | 25058 | | | | 147 |

AMPS: 2-Acrylamido-2-methylpropanesulfonic acid
MBAm: N,N'-ethylenebisacrylamide

Example 3: Scaling of a Test Adsorber which has a Differing Size-Exclusion Limit in Relation to the Process Adsorber In Table 1 above, the scaling factors arising from the binding capacities of the BCA assay are already presented. The practical application of said factors will be described below.

Filtration of a Human IgG Protein Solution Across Various Polyamide Prefilters:

For the filtration, use was made of a solution of a human IgG (5% solution, SeraCare, catalog No. HS-475-1 L) which was diluted with a 50 mM KPI buffer solution, pH 7.2, to a concentration of 0.5%.

Membranes Used:
Prefilter (VF)$_1$: Nylon 6
Nominal pore size: 0.35 μm
Flow time for water [ml/(min cm$^2$ bar)]: 23
Bubble point with water, visual [bar]: 2.9
Prefilter (VF)$_2$: Nylon 6
Nominal pore size: 0.1 μm
Flow time for water [ml/(min cm$^2$ bar)]: 6
Bubble point with water, visual [bar]: 7
End filter (EF): surface-modified, virus-retentive polyethersulfone Virosart® HC membrane (surface-modified polyethersulfone membrane having a nominal pore size of 20 nm), double layer
Nominal pore size: 20 nm
Flow time for water [ml/(min cm$^2$ 2 bar)]: 0.19
Effective incident-flow area: 4.7 cm$^2$ Both filtrations were operated "in-line", i.e., VF and EF were connected to one another via the Luer connector before the start of filtration. The VF$_1$ module has an effective incident-flow area of 4.7 cm$^2$, whereas the VF$_2$ module has an effective incident-flow area of 3.11 cm$^2$.

The filtrations were carried out in parallel with the same stock solution and under a pressure of 2 bar. The different slopes in FIGS. 5 and 6 are caused by the differing flow resistance of the two adsorbers.

Figure 5:
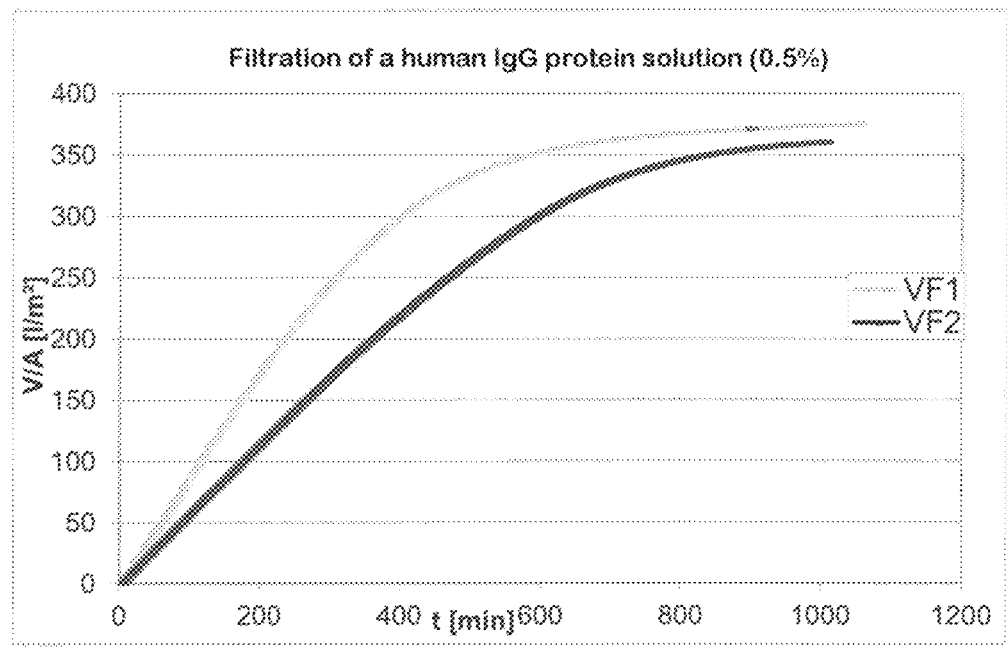
Figure 6:
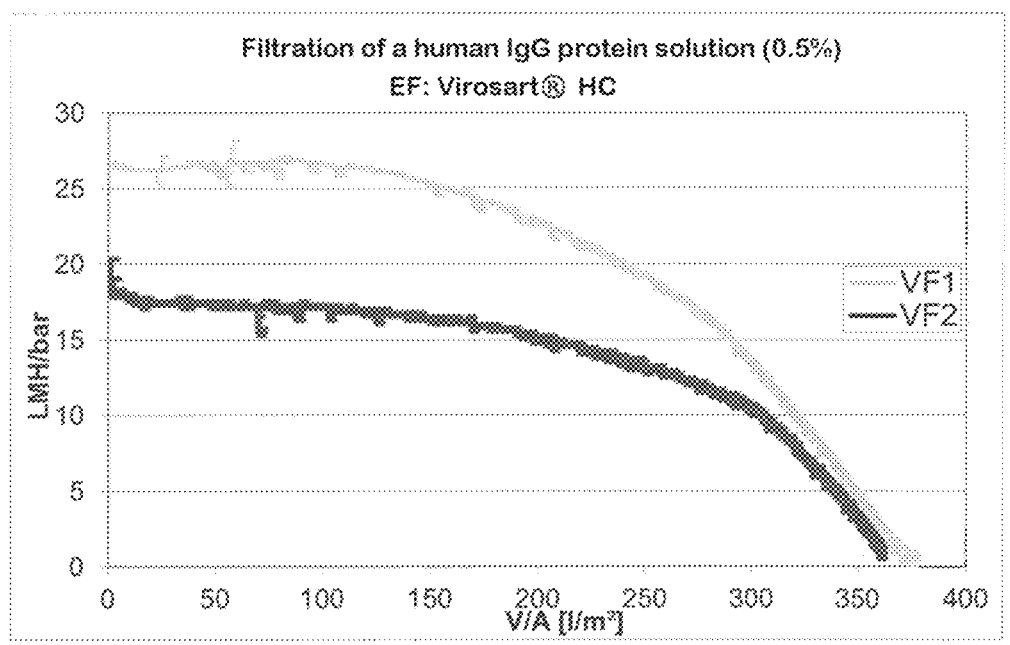

FIGS. 5 and 6 show that the filtered volume is virtually identical for the two filtrations, because the adsorber quantity used, referred to here as VF1 and VF2, was scaled such that the same binding capacity for impurities was achieved.

Owing to the appropriate scaling of the membrane areas of the prefilters, an approximately identical service life was achieved.

Selection Criteria for the Area Scaling of the Prefilters:

One way of measuring the nonspecific protein adsorption of a membrane is found in the BCA method. In said method, the protein adsorbs to a membrane and is quantitatively determined photometrically using BCA reagent (2,2-biquinoline-4,4-dicarboxylic acid disodium salt dihydrate).

The following results were ascertained in this connection:
VF$_1$: 52.7 μg/cm$^2$
VF$_2$: 84.2 μg/cm$^2$ To then arrive at an identical adsorption during the filtration, the area of the VF$_1$ had to be enlarged by a factor of 1.6.

The invention claimed is:
1. A method for determining the logarithmic reduction value LRV$_{Size\text{-}exclusion\ filter}$ of a size-exclusion filter G for a particle of a process solution, which particle is to be clarified, the size-exclusion filter G being protected from a blocking adsorbing species present in the process solution by a process adsorber P connected upstream in series and the particle to be clarified being retained by the process adsorber P with an $LRV_{Process\ absorber}$ of 0.5 or more, comprising the steps of:

(a) providing a test system comprising
a size-exclusion filter G, the $LRV_{Size-exclusion\ filter}$ of which is to be determined, and
a test adsorber T which is connected upstream of the size-exclusion filter G in series and which consists of a similar material to the process adsorber P and which retains the particle to be clarified with a known $LRV_{Test\ adsorber}$ of 2 or less, where $LRV_{Test\ adsorber} < LRV_{Process\ adsorber}$;

(b) determining $LRV_{Test\ system}$ of the test system for the particle to be clarified; and (c) calculating $LRV_{Size-exclusion\ filter}$ by subtracting the $LRV_{Test\ adsorber}$ from $LRV_{Test\ system}$, wherein the process adsorber P has a specific adsorption capacity $k_1$, is present on a scale $M_1$ and has a total adsorption capacity of $k_1 \times M_1$, wherein the test adsorber T has a specific adsorption capacity $k_2$, is present on a scale $M_2$ and has a total adsorption capacity of $k_2 \times M_2$, where $$0.1 < \frac{k_1 M_1}{k_2 M_2} < 10,$$

wherein the total adsorption capacities of the process adsorber P and of the test adsorber T are determined by gas sorption measurement, by determination of breakthrough curves, by binding experiments with model proteins or by static incubation, and wherein $$LRV = \log \frac{C_{feed}}{C_{filtrate}}$$

and $C_{feed}$ is the concentration of the particle to be filtered out in the process solution before passage through a filter and $C_{filtrate}$ is the concentration of the particle to be filtered out in the process solution after passage through the filter.

2. The method as claimed in claim 1, wherein the test adsorber T has an $LRV_{Test\ adsorber}$ of 1 or less.

3. The method as claimed in claim 1, where $$0.5 < \frac{k_1 M_1}{k_2 M_2} < 5.$$

4. The method as claimed in claim 1, where $$0.9 < \frac{k_1 M_1}{k_2 M_2} < 1.1.$$

5. The method as claimed in claim 1, wherein the process adsorber P and the test adsorber T are present as mechanically integral shaped bodies.

6. The method as claimed in claim 5, wherein the process adsorber (P) and the test adsorber T are present in the form of membranes.

7. The method as claimed in claim 6, wherein the blocking adsorbing species is a blocking adsorbing species selected from biopolymers, biopolymer aggregates, biological particles, viral vectors, viruses and microorganisms.

* * * * *